United States Patent
Baroud

(10) Patent No.: US 8,070,728 B2
(45) Date of Patent: Dec. 6, 2011

(54) CANNULA ASSEMBLY WITH DETACHABLE INNER AND OUTER CANNULAS

(75) Inventor: Gamal Baroud, Canton-de-Hatley (CA)

(73) Assignee: Societe de Commercialisation des produits de la recherche appliquee socpra sciences et genie s.e.c, Montreal, Quebec (CA)

( * ) Notice: Subject to any disclaimer, the term of this patent is extended or adjusted under 35 U.S.C. 154(b) by 0 days.

(21) Appl. No.: 12/453,261

(22) Filed: May 5, 2009

(65) Prior Publication Data

US 2010/0286616 A1 Nov. 11, 2010

(51) Int. Cl.
*A61M 5/178* (2006.01)

(52) U.S. Cl. .................................. 604/164.01

(58) Field of Classification Search ............... 604/93.01, 604/158, 160, 161, 162, 164.01, 164.04, 604/164.06, 164.1, 164.11, 164.12, 165.01, 604/167.01, 23, 24, 541, 542, 533, 534, 535

See application file for complete search history.

(56) References Cited

U.S. PATENT DOCUMENTS

| | | | |
|---|---|---|---|
| 4,099,528 A | 7/1978 | Sorenson et al. | |
| 4,180,068 A | 12/1979 | Jacobsen et al. | |
| 4,202,332 A | 5/1980 | Tersteegen et al. | |
| 5,012,818 A | 5/1991 | Joishy | |
| 6,419,654 B1 * | 7/2002 | Kadan | 604/27 |
| 6,979,352 B2 | 12/2005 | Reynolds | |
| 7,112,205 B2 | 9/2006 | Carrison | |
| 7,153,307 B2 | 12/2006 | Scribner et al. | |
| 7,572,263 B2 | 8/2009 | Preissman | |
| 2004/0097880 A1 * | 5/2004 | Schur | 604/164.01 |
| 2004/0167473 A1 * | 8/2004 | Moenning | 604/164.02 |
| 2008/0119821 A1 * | 5/2008 | Agnihotri et al. | 604/513 |
| 2009/0198242 A1 | 8/2009 | Truckai et al. | |

* cited by examiner

Primary Examiner — Christopher D Koharski
(74) Attorney, Agent, or Firm — Norton Rose OR LLP

(57) ABSTRACT

A cannula assembly for injecting implant material into a bone, including an inner cannula defining a central conduit including a first proximal port in communication with the central conduit, an outer cannula surrounding the inner cannula to define a peripheral conduit, and a connector interconnecting the cannulas and detachable from at least one of the cannulas, and at least one of the connector, the first cannula and the second cannula including a second proximal port in communication with the peripheral conduit defined along a direction different than a longitudinal axis of the first and second cannulas.

15 Claims, 12 Drawing Sheets

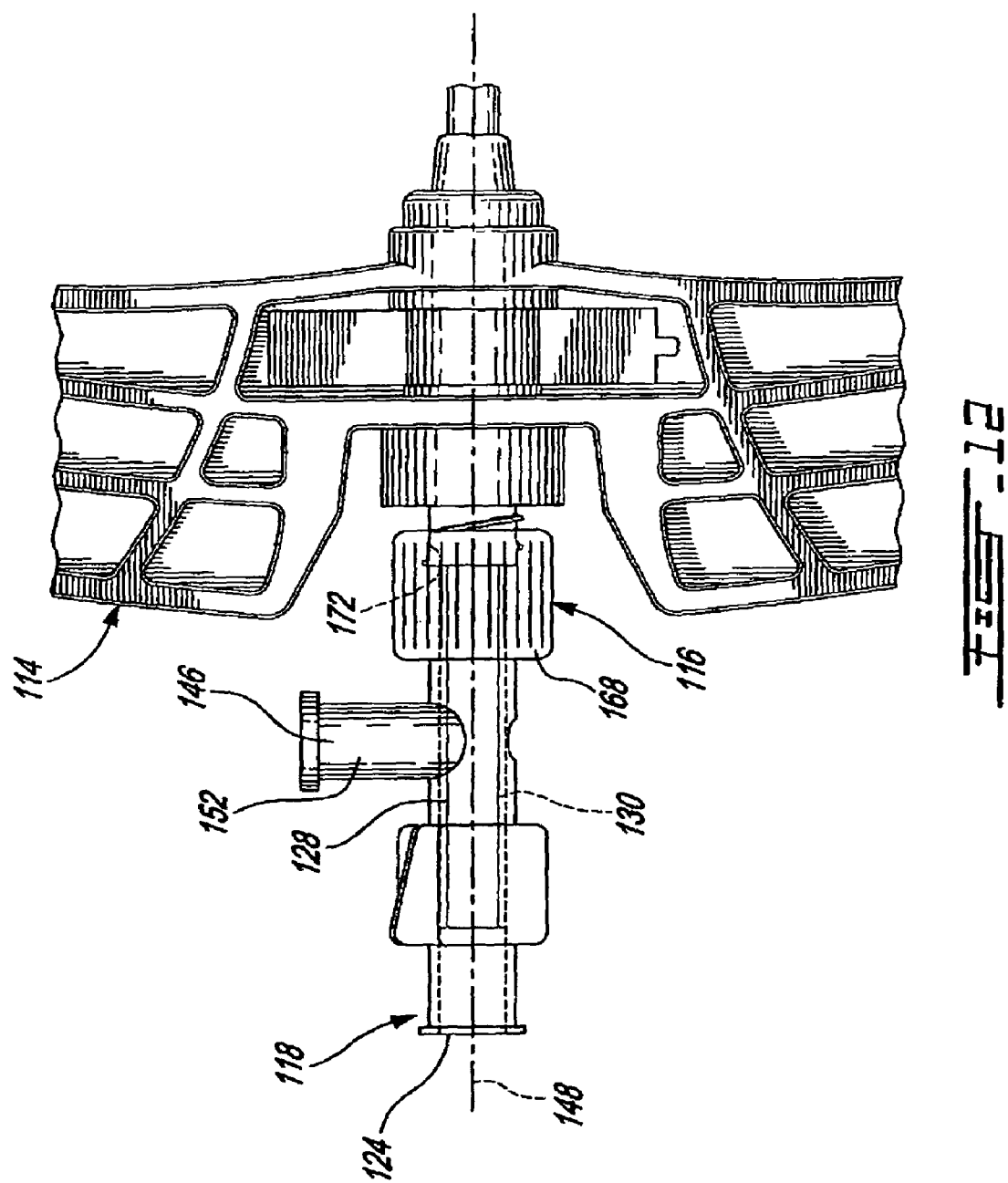

CANNULA ASSEMBLY WITH DETACHABLE INNER AND OUTER CANNULAS

FIELD OF THE INVENTION

This invention relates to a system for bone augmentation and more particularly to a double lumen cement delivery cannula.

BACKGROUND ART

Vertebral body augmentation procedures have evolved for the treatment of vertebral fractures (VCF), which are the most common type of skeletal fracture related to osteoporosis.

Vertebroplasty has been developed to treat vertebral compression fractures, and consists of injecting medical bone cement under pressure through a cannula into a vertebral body. The bone is usually porous with bone marrow occupying the porous space. The cement injected into the vertebral body displaces the bone marrow and fills the bone cavity. The cement hardens in-situ, providing mechanical strength and stability of the bone weakened by osteoporosis or other pathologies such as cancers.

Vertebroplasty is usually performed using a cannula including one lumen through which a stylet is inserted to facilitate access of the cannula to the injection site. Once the cannula is in place, the stylet is removed and bone cement is injected through the lumen. It is also known to use a second cannula placed near the cement injection cannula to aspirate bone fluid.

Catheters and cannulas having double lumens are generally known and used for various medical purposes, such as for example hemodyalisis. Typically, such catheters and cannulas are integrally formed in one piece, or are formed from two or more elements which are permanently attached together.

Accordingly, improvements are desirable.

SUMMARY

It is therefore an aim of the present invention to provide an improved cannula for injection of implant material into a bone, which in a particular embodiment is used for vertebroplasty.

Therefore, in accordance with the present invention, there is provided a cannula assembly for injecting implant material into a bone, the assembly comprising an inner cannula having a first proximal end and a first tube extending from the proximal end, the first tube defining a central conduit and including at least one first distal opening in communication with the central conduit, the first proximal end including a first proximal port in communication with the central conduit, an outer cannula having a second proximal end and a second tube extending from the proximal end, the second tube having a larger inner diameter than that of the first tube, the second tube surrounding the first tube in a concentric manner such that a peripheral conduit is defined between the first and second tubes, the second tube including at least one second distal opening in communication with the peripheral conduit, a connector interconnecting the first and second proximal ends, the connector being detachable from at least one of the first and second proximal ends to allow the inner and outer cannulas to be disconnected from one another, and at least one of the connector, the first cannula and the second cannula including at least one second proximal port in communication with the peripheral conduit, the at least one second proximal port being defined along a direction different than a longitudinal axis of the first and second cannulas.

Also in accordance with the present invention, there is provided a method for placing a double lumen cannula into a bone for implant injection, the method comprising inserting a stylet into a conduit of an outer cannula, inserting the stylet and outer cannula simultaneously into the bone, removing the stylet from the conduit of the outer cannula, inserting an inner cannula having a first lumen into the conduit of the outer cannula to define a second lumen between the inner and outer cannulas, and detachably interconnecting the inner and outer cannulas such that the connected first and second cannulas define a first distal port in communication with the first lumen and a second distal port in communication with the second lumen.

BRIEF DESCRIPTION OF THE DRAWINGS

Reference will now be made to the accompanying drawings, showing by way of illustration a particular embodiment of the present invention and in which:

FIG. 12 is a side view of a proximal part of an engaged inner and outer cannulas of the cannula assembly of FIG. 9.

DETAILED DESCRIPTION OF PARTICULAR EMBODIMENTS

Figure 1:
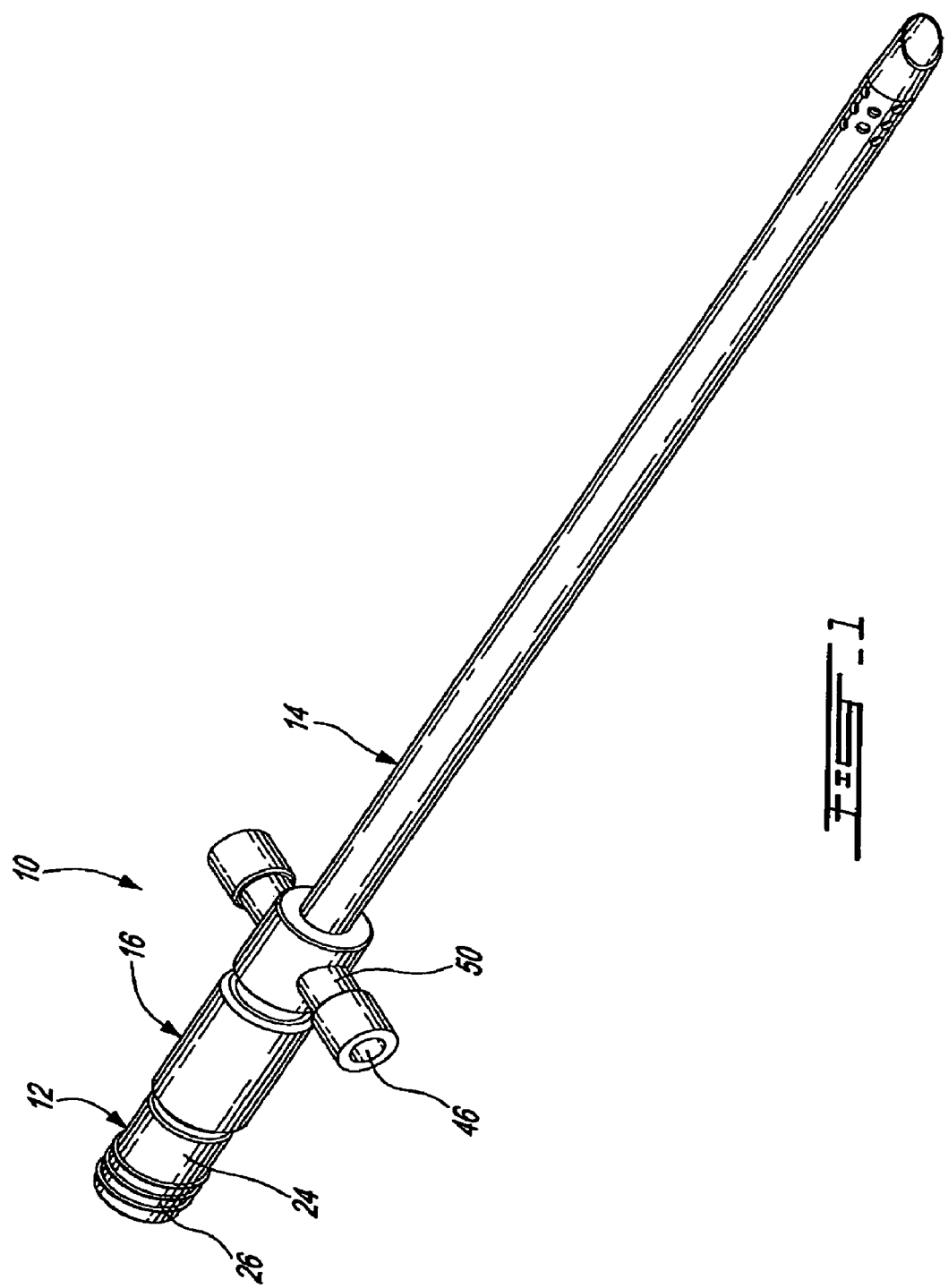
FIG. 1 is a perspective view of a cannula assembly according to a particular embodiment of the present invention.

Referring to FIG. 1, a cannula assembly 10 is shown. The cannula assembly 10 includes an inner cannula 12, an outer cannula 14, and a connector or fastener 16 detachably interconnecting the inner and outer cannulas 12, 14.

Figure 2:
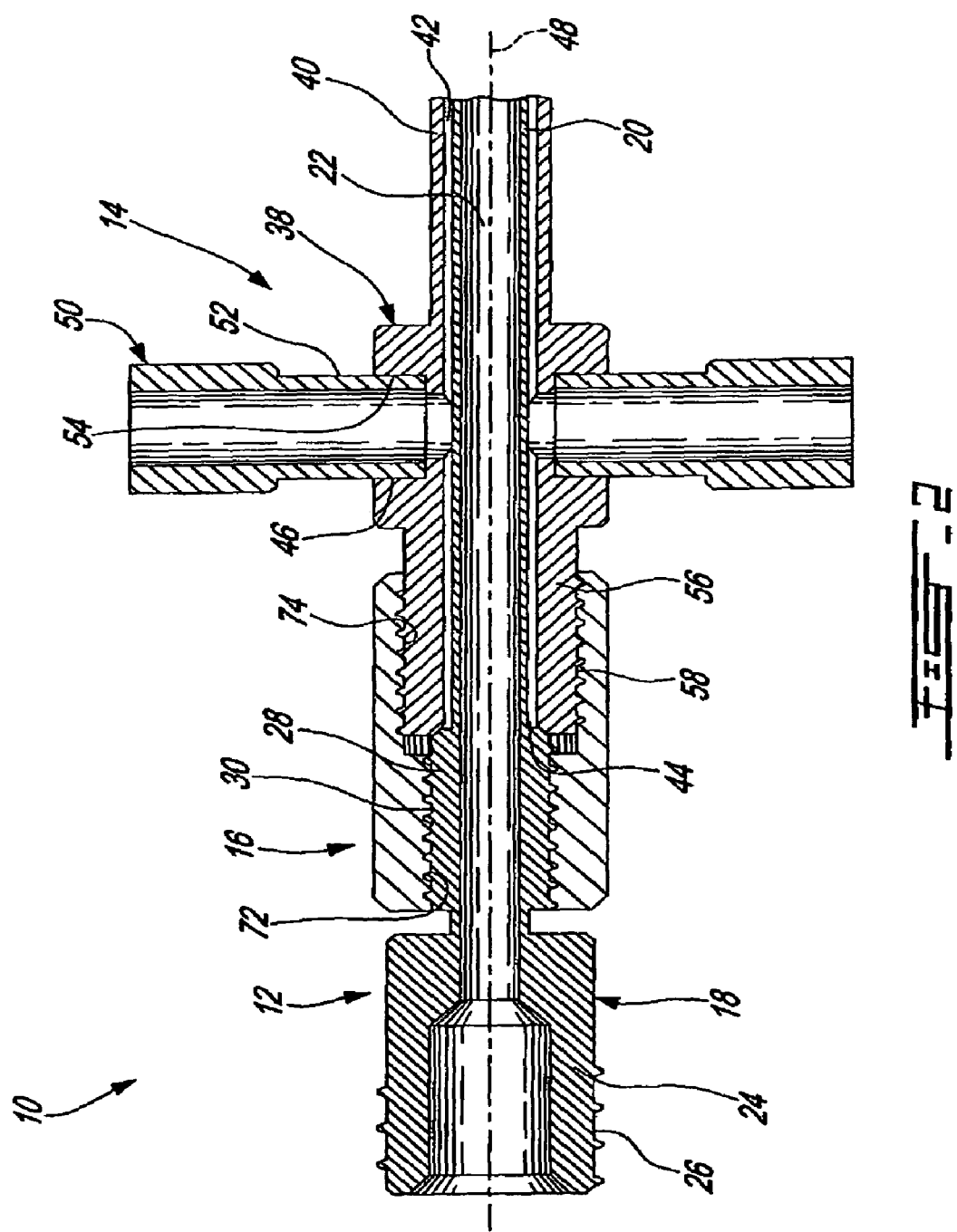
FIG. 2 is a cross-sectional view of a proximal part of the cannula assembly of FIG. 1.
Figure 7:
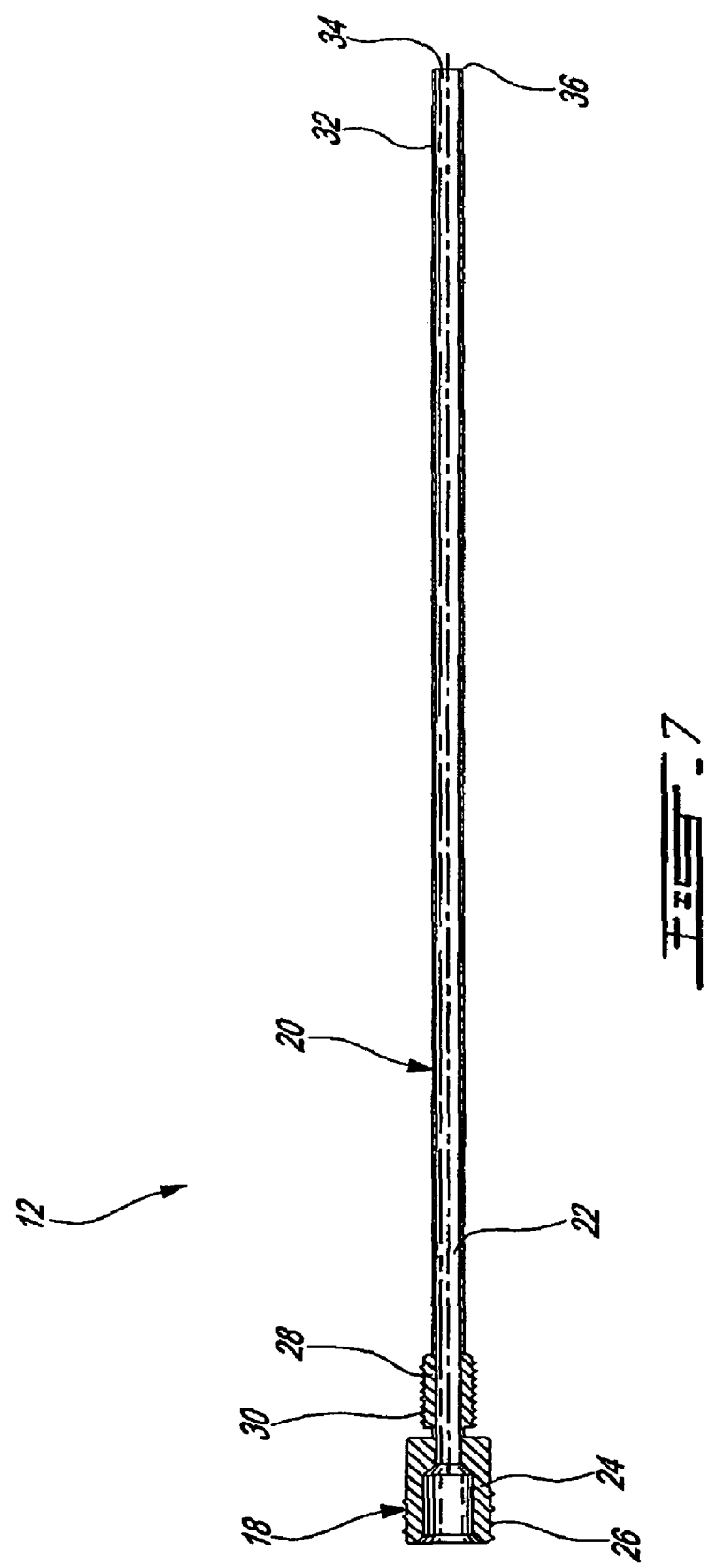
FIG. 7 is a cross-sectional view of an inner cannula of the cannula assembly of FIG. 1.

Referring to FIGS. 2 and 7, the inner cannula 12 includes a proximal end 18 and a tube 20 extending therefrom. The tube 20 defines a central conduit 22 extending therethrough. The proximal end 18 defines a proximal axial port 24 in communication with the central conduit 22. The axial port 24 includes a threaded outer surface 26, which in a particular embodiment forms a standard female luer thread, such as to be connectable e.g. to an injection device for injecting an implant material or to a vacuum device to provide aspiration through the central conduit. Alternately, the threaded outer surface 26 can be replaced by any adequate type of connection member, depending on the device to be connected to the inner cannula 12, and/or the proximal port 24 can have a different orientation, e.g. can extend radially.

The proximal end 18 of the inner cannula 12 also includes an engagement portion 28 having an enlarged diameter with respect to a remainder of the tube 20, located distally of the proximal port 24. The engagement portion 28 has an outer surface 30 that is threaded for engagement with the connector 16, as will be further detailed below.

Figure 3:
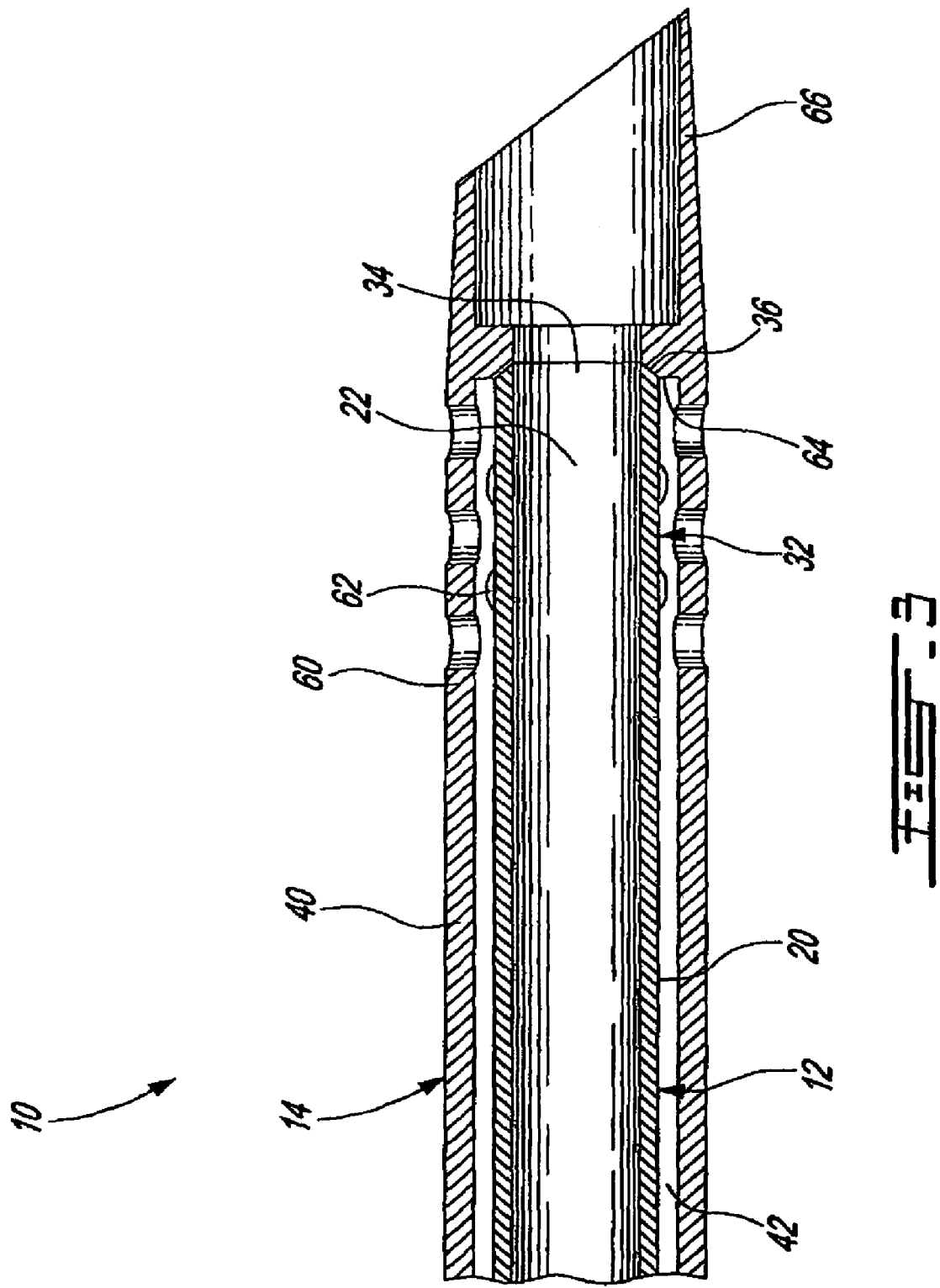
FIG. 3 is a cross-sectional view of a distal part of the cannula assembly of FIG. 1.

Referring to FIGS. 3 and 7, the inner cannula 12 also includes a distal end 32 defining at least one distal opening 34 in communication with the central conduit 22. In the embodiment shown, the distal opening 34 corresponds to the open distal tip 36 of the inner cannula 12. Alternate embodiments which are not shown include the inner cannula having side distal openings defined through the wall of the inner tube, in addition or in replacement of having an open distal tip.

Referring back to FIG. 2, the outer cannula 14 includes a proximal end 38 and a tube 40 extending therefrom, the tube 40 of the outer cannula 14 having an inner diameter larger than the outer diameter of the tube 20 of the inner cannula 12. The tube 40 of the outer cannula 14 surrounds the tube 20 of the inner cannula 12 in a concentric manner, such that a peripheral conduit 42 is defined therebetween. As can also be seen in FIGS. 4-5, the proximal end 38 of the outer cannula 14 includes a proximal axial port 44 through which the inner cannula 12 is inserted.

The proximal end 38 of the outer cannula 14 also defines two proximal side ports 46 in communication with the peripheral conduit 42. In the embodiment shown, the side ports 46 are defined along a same direction with opposite orientations, perpendicularly to the longitudinal axis 48 of the cannulas 12, 14. Referring back to FIG. 2, the outer cannula 14 also includes a sleeve 50 removably engaged with each side port 46 of the outer tube 40, which in the example shown is done by having an outer surface 52 of each sleeve 50 threadably engaged with an inner surface 54 of the respective side port 46. The outer surface 52 of each sleeve 50 is also shaped to engage e.g. an injection device for injecting an implant material or a vacuum device to provide aspiration through the peripheral conduit. Alternate embodiments which are not shown include embodiments where the sleeves are integral with the outer tube, where a single side port is provided, and/or where the side ports extend at an angle different than the perpendicular to the longitudinal axis.

The proximal end 38 of the outer cannula 14 also includes an engagement portion 56 located proximally of the side ports 46 and defining an outer surface 58 which is threaded for engagement with the connector 16, as will be further detailed below.

Figure 4:
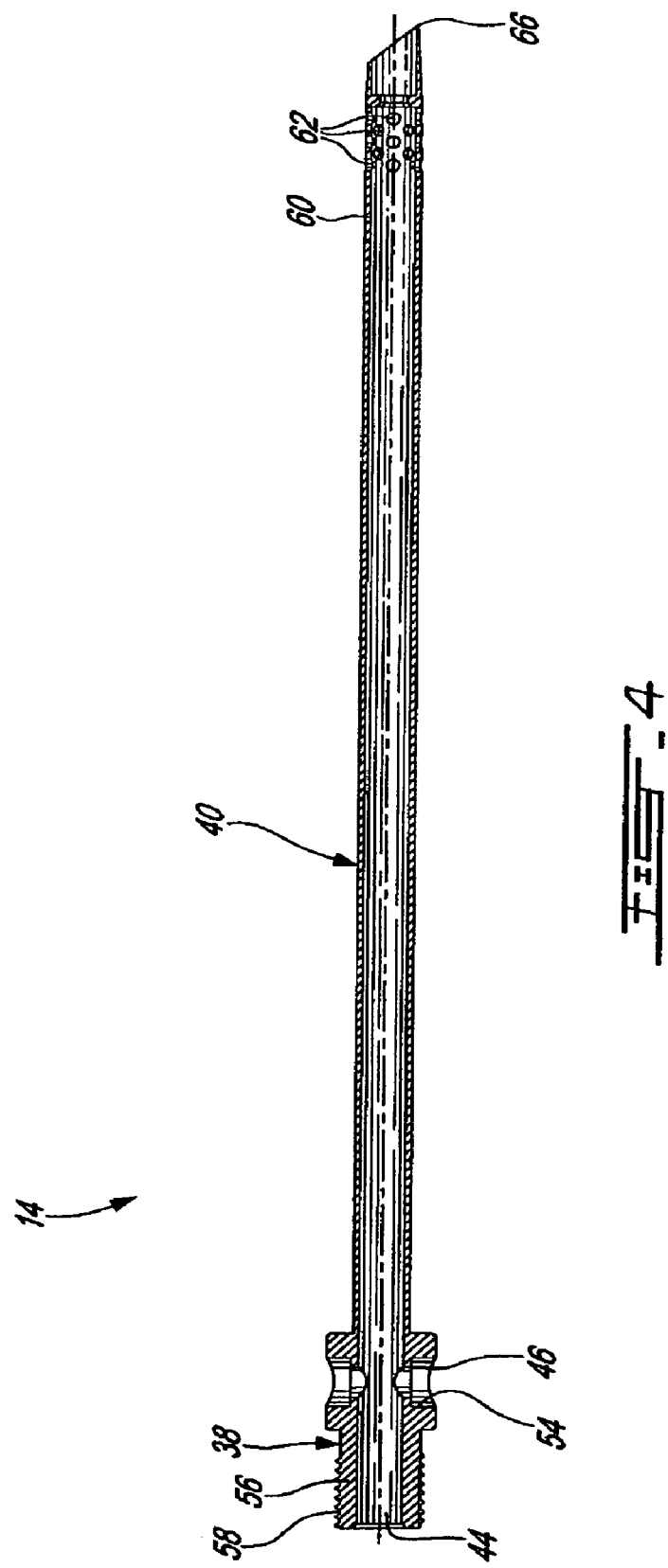
FIG. 4 is a cross-sectional view of an outer cannula of the cannula assembly of FIG. 1.
Figure 5:
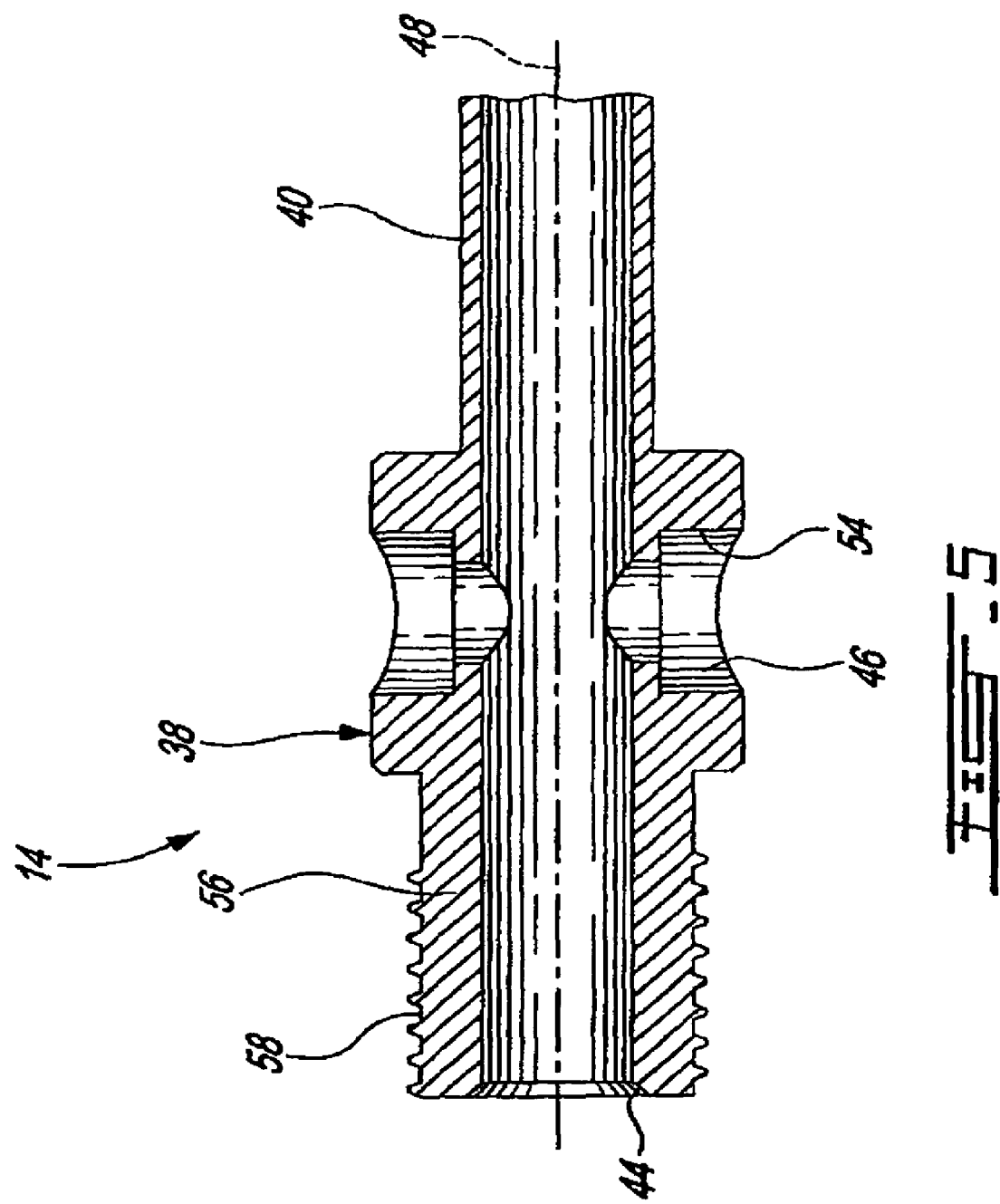
FIG. 5 is a cross-sectional view of a proximal part of the outer cannula of FIG. 4.
Figure 6:
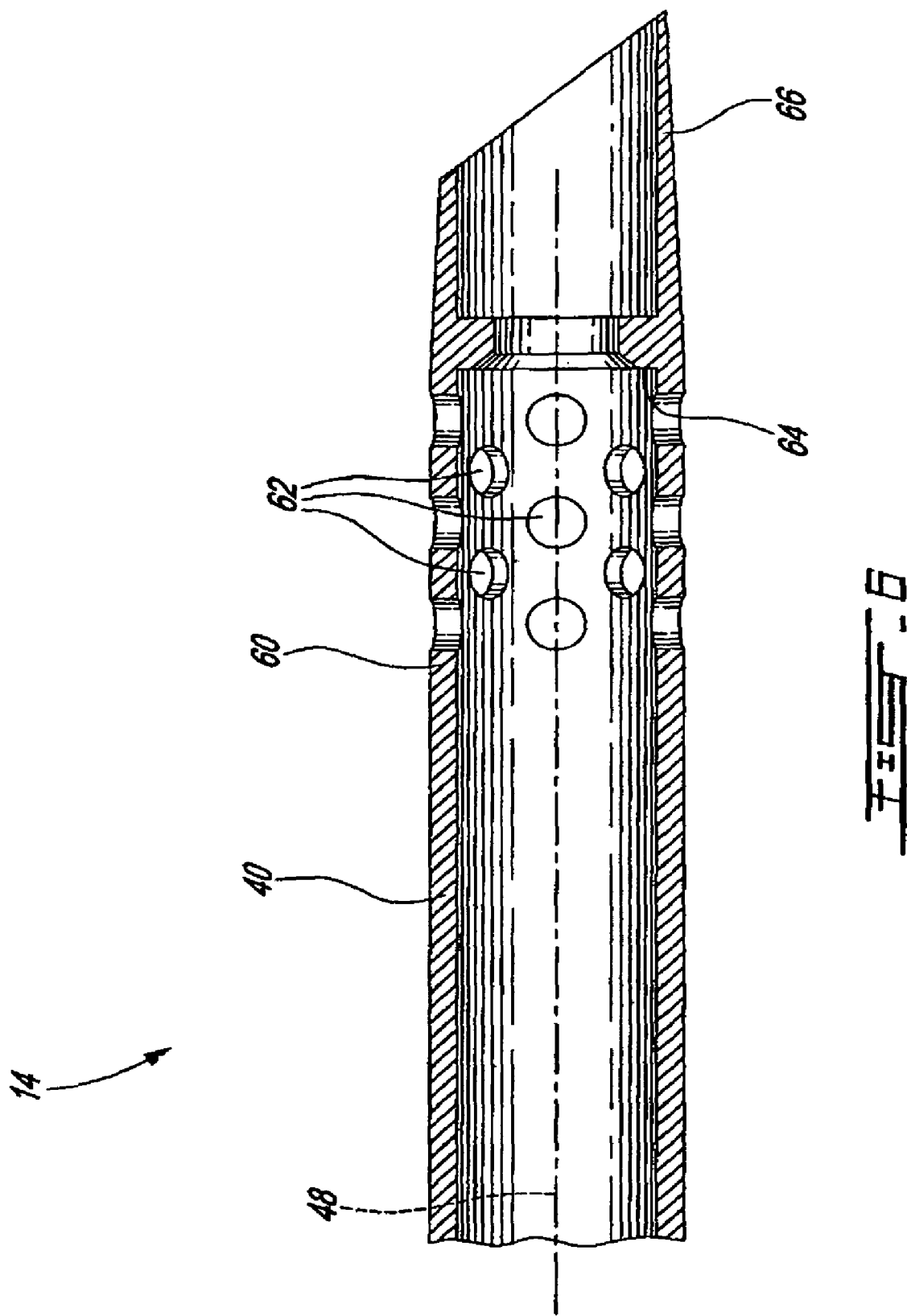
FIG. 6 is a cross-sectional view of a distal part of the outer cannula of FIG. 4.

Referring to FIGS. 3, 4 and 6, the outer cannula 14 includes a distal end 60 defining at least one distal opening 62 in communication with the peripheral conduit 42. In the embodiment shown, the outer cannula 14 includes a plurality of distal openings or fenestrations 62 defined through the wall of the outer tube 40. The fenestrations 62 are distributed around a circumference of the outer tube 40, and in the embodiment shown, are circular. Alternate shapes include, but are not limited to, oval and rectangular openings.

As can be seen in FIG. 3, the outer tube 40 defines an inner shoulder 64 extending within the peripheral conduit 42, and the distal tip 36 of the inner tube 20 abuts that shoulder 64 to at least substantially close, and in a particular embodiment seal, the distal tip of the peripheral conduit 42. The distal tip 66 of the outer-tube 40 is open and forms the open distal end of the central conduit 22.

Figure 8:
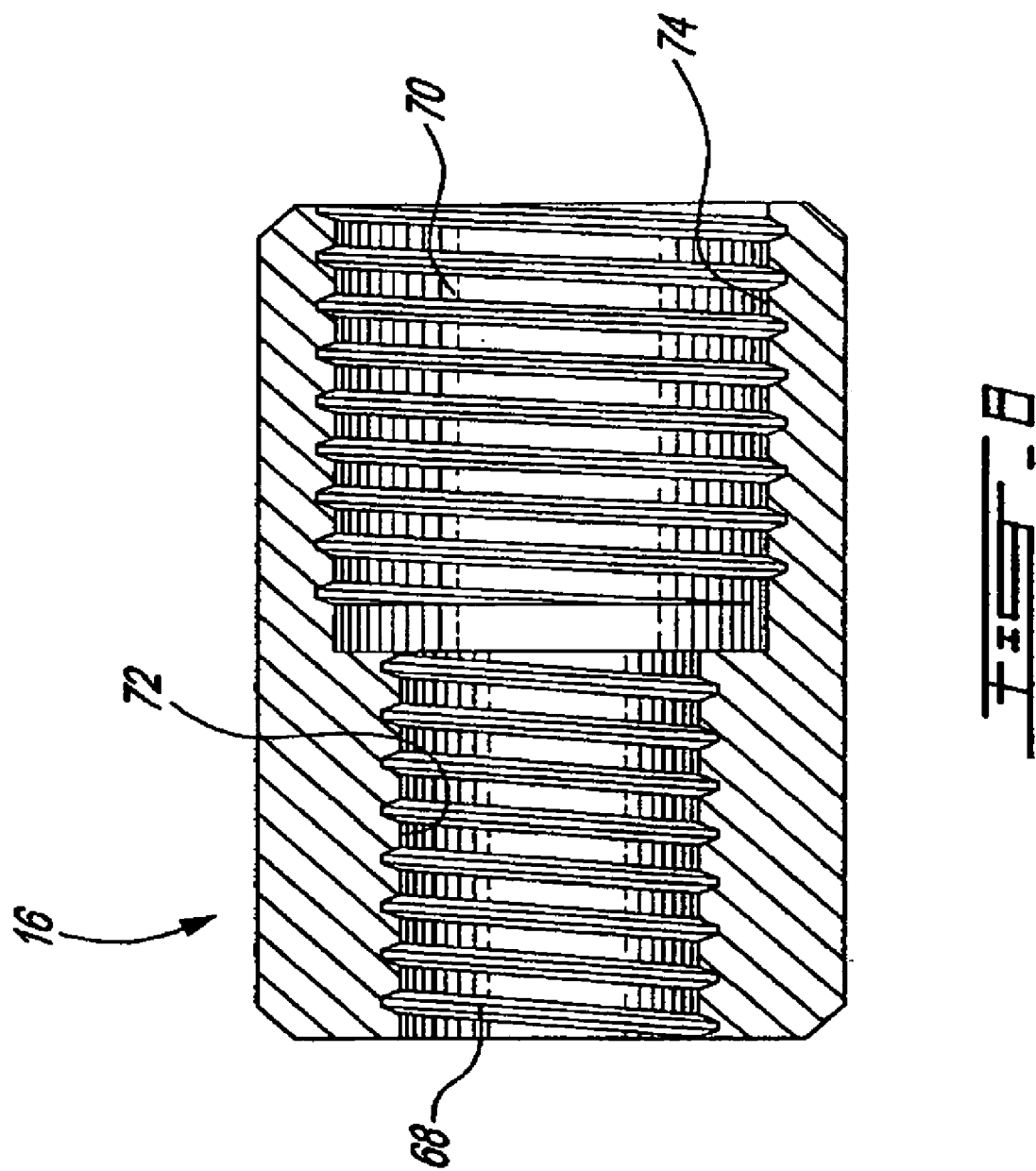
FIG. 8 is a cross-sectional view of a connector of the cannula assembly of FIG. 1.

Referring to FIGS. 3 and 8, the connector 16 has the form of a sleeve, with first and second passages 68, 70 extending therethrough in alignment and in communication with one another. The first and second passages 68, 70 have different diameters, and each includes a threaded inner surface 72, 74. Referring to FIG. 2, the externally threaded engagement portion 56 of the outer cannula 14 defines the extremity of the outer cannula 14, and the externally threaded engagement portion 28 of the inner cannula 12 is sized such as to abut the extremity of the outer cannula 14 when the inner cannula 12 is inserted therein. The first and second passages 68, 70 of the connector are sized and configured to threadably engage the threaded outer surfaces 30, 58 of the engagement portions 28, 56 of a respective one of the inner and outer cannulas 12, 14. As such, the connector 16 detachably interconnects the inner and outer cannulas 12, 14.

The detachable inner and outer cannulas 12, 14 thus allow for the selective formation of a double lumen cannula. In addition, the assembly can further include a stylet (not shown) which can be inserted into the outer cannula 14 to facilitate placement into the bone, and then be removed and replaced by the inner cannula 12 such that the double lumen cannula is provided.

Figure 9:
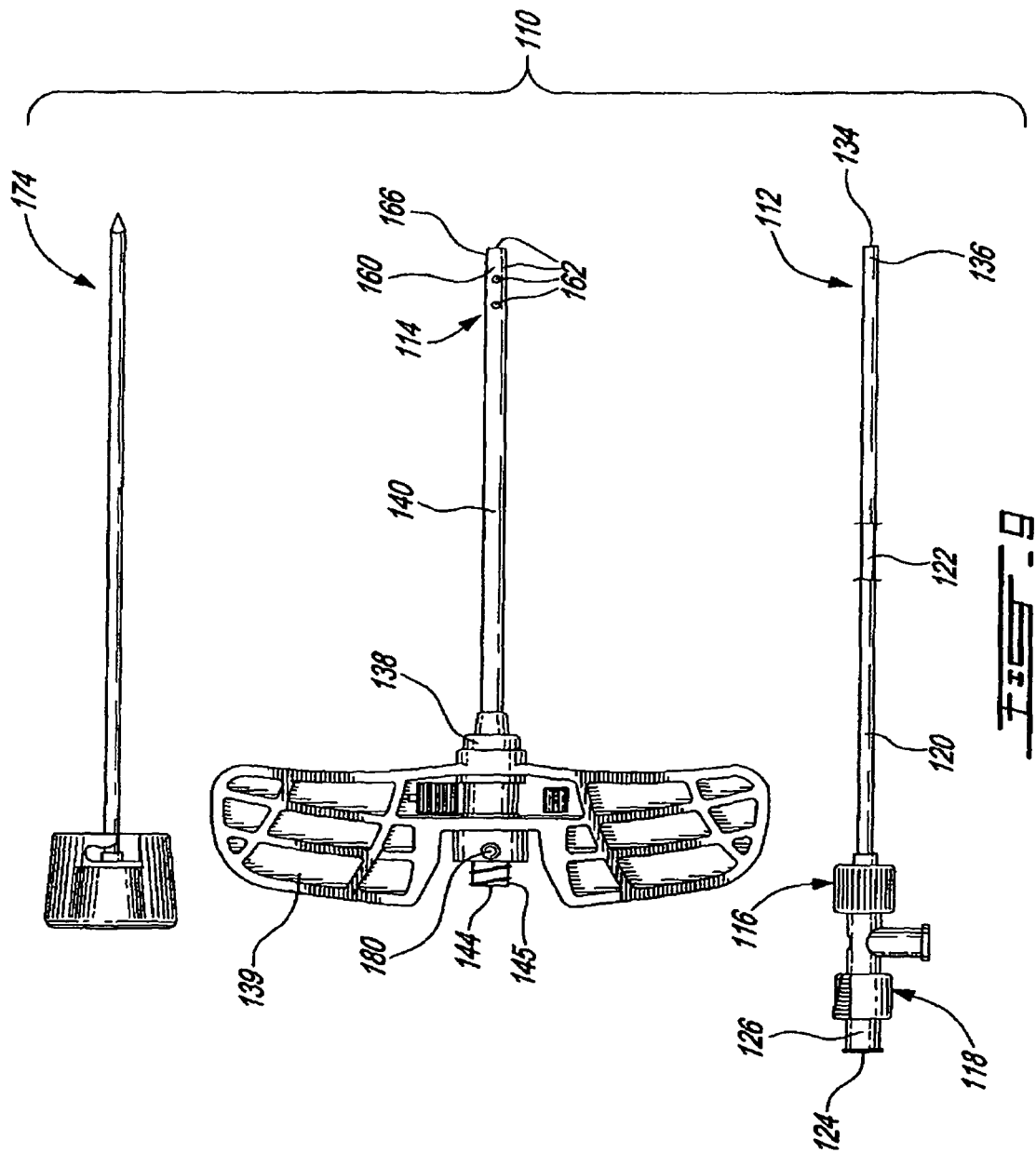
FIG. 9 is a side view of components of a cannula assembly in accordance with an alternate embodiment.

Referring to FIG. 9, a cannula assembly 110 according to an alternate embodiment is shown. The cannula assembly 110 includes an inner cannula 112, an outer cannula 114, a connector or fastener 116 detachably interconnecting the inner and outer cannulas 112, 114, and a stylet 174.

As with the previous embodiment, the inner cannula 112 includes a proximal end 118 and a tube 120 extending therefrom. The tube 120 defines a central conduit 122 extending therethrough, and the proximal end 118 defined a proximal axial port 124 in communication with the central conduit 122. The outer surface 126 of the axial port 124 is shaped and configured such as to be connectable e.g. to an injection device for injecting an implant material or to a vacuum device to provide aspiration through the central conduit. Alternately, the proximal port 124 can have a different orientation, e.g. can extend radially.

As can be best seen in FIG. 12, the proximal end 118 of the inner cannula 112 includes an outer tubular portion 128 surrounding the inner tube 120, such as to define a peripheral conduit portion 130 therearound. The outer tubular portion 128 includes a proximal side port 146 extending therethrough in communication with the peripheral conduit portion 130. In the embodiment shown, the side port 146 is defined perpendicularly to the longitudinal axis 148 of the cannulas 112, 114. The side port 146 has an outer surface 152 shaped and configured to engage e.g. an injection device for injecting an implant material or to a vacuum device to provide aspiration through the peripheral conduit portion. Alternate embodiments which are not shown include embodiments where more than one side port is provided, and/or where the side port(s) extend at an angle different than the perpendicular to the longitudinal axis.

Referring back to FIG. 9, the inner cannula 112 includes an open distal tip 136, forming a distal opening 134 in communication with the central conduit 122. Alternate embodiments which are not shown include inner cannulas including side distal openings defined through the wall of the inner tube, in addition or in replacement of having an open distal tip.

Figure 11:
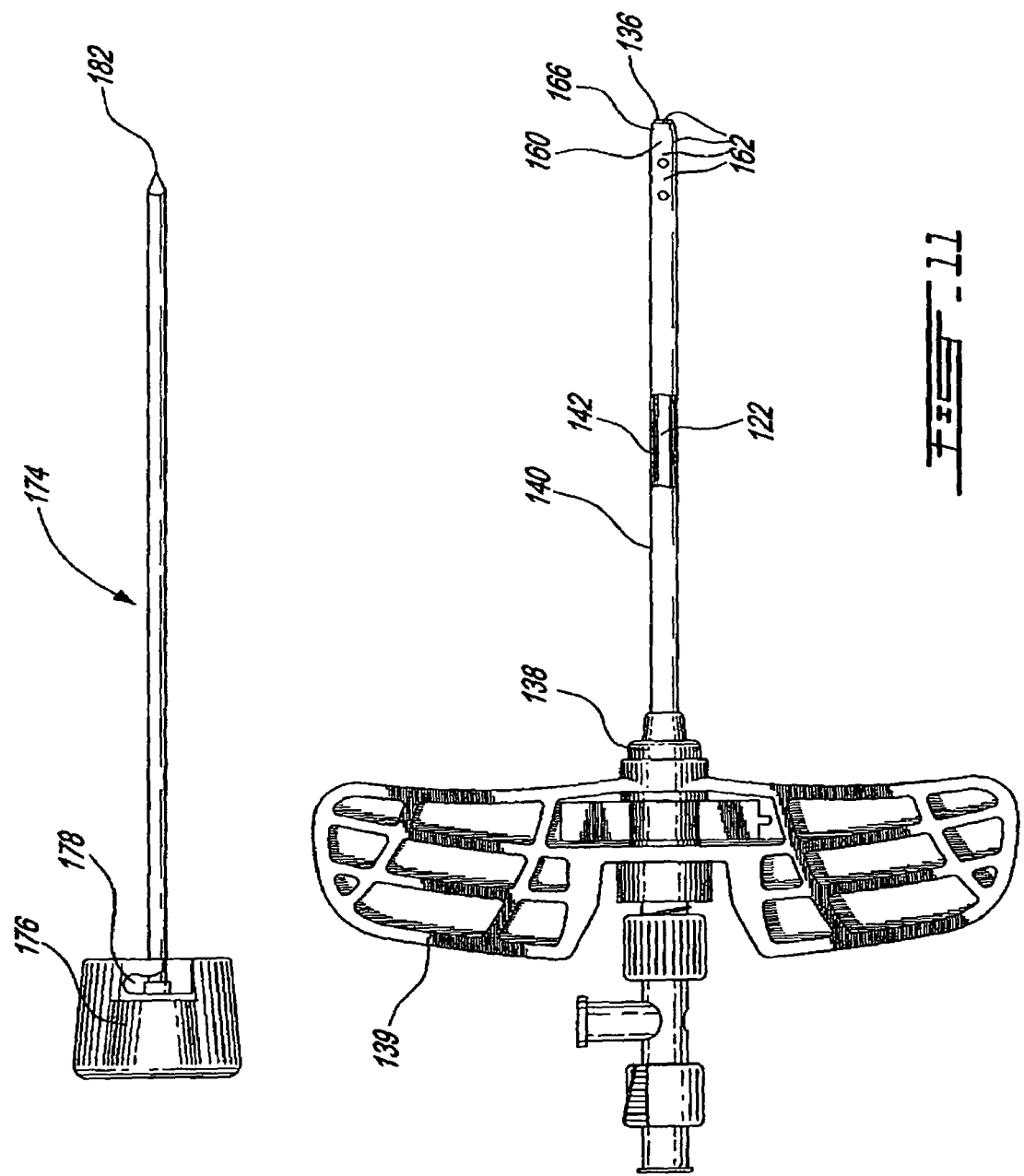
FIG. 11 is a side view of engaged inner and outer cannulas of the cannula assembly of FIG. 9, also showing a stylet thereof.

Referring to FIGS. 9 and 11, the outer cannula 114 includes a proximal end 138 around which a handle 139 is detachably connected to facilitate gripping, and a tube 140 extending therefrom having an inner diameter larger than the outer diameter of the tube 120 of the inner cannula 112. The tube 140 of the outer cannula 114 surrounds the tube 120 of the inner cannula 112 in a concentric manner, such that a peripheral conduit 142 (see FIG. 11) is defined therebetween. The proximal end 138 of the outer cannula 114 includes a proximal axial port 144 through which the inner cannula 112 is inserted.

The outer cannula 114 includes a distal end 160 including a plurality of distal openings or fenestrations 162 defined through the wall of the outer tube 140 and in communication with the peripheral conduit 142. The fenestrations 162 are distributed around a circumference of the outer tube 140, and in the embodiment shown, are circular. Alternate shapes include, but are not limited to, oval and rectangular openings. The distal tip 166 of the outer tube 140 is open and defines another distal opening 162 in communication with the peripheral conduit 142. As can be seen in FIG. 9, the distal tip 136 of the inner cannula 112 extends beyond the distal tip 166 of the outer cannula 114 when the two cannulas are assembled.

As can be seen more clearly on FIG. 9, the connector 116 is provided on the inner cannula 112. Referring to FIG. 12, the connector 116 includes a sleeve 168 which is retained around a distal end of the tubular portion 128 such as to be rotatable relative thereto. The sleeve 168 has a threaded inner surface 172. As can be seen in FIG. 9, an outer surface 145 of the axial port 144 of the outer cannula 114 is also correspondingly threaded, and as such the sleeve 168 is threadably engaged to the axial port 144 of the outer cannula 114 to retain the cannulas 112, 114 together. The sleeve 168 also provides communication between the peripheral conduit portion 130 defined by the tubular portion 128 of the inner cannula 112 and the peripheral conduit 142 defined between the inner and outer cannulas 112, 114.

As in the previous embodiment, the detachable inner and outer cannulas 112, 114 thus allow for the selective formation of a double lumen cannula.

Figure 10:
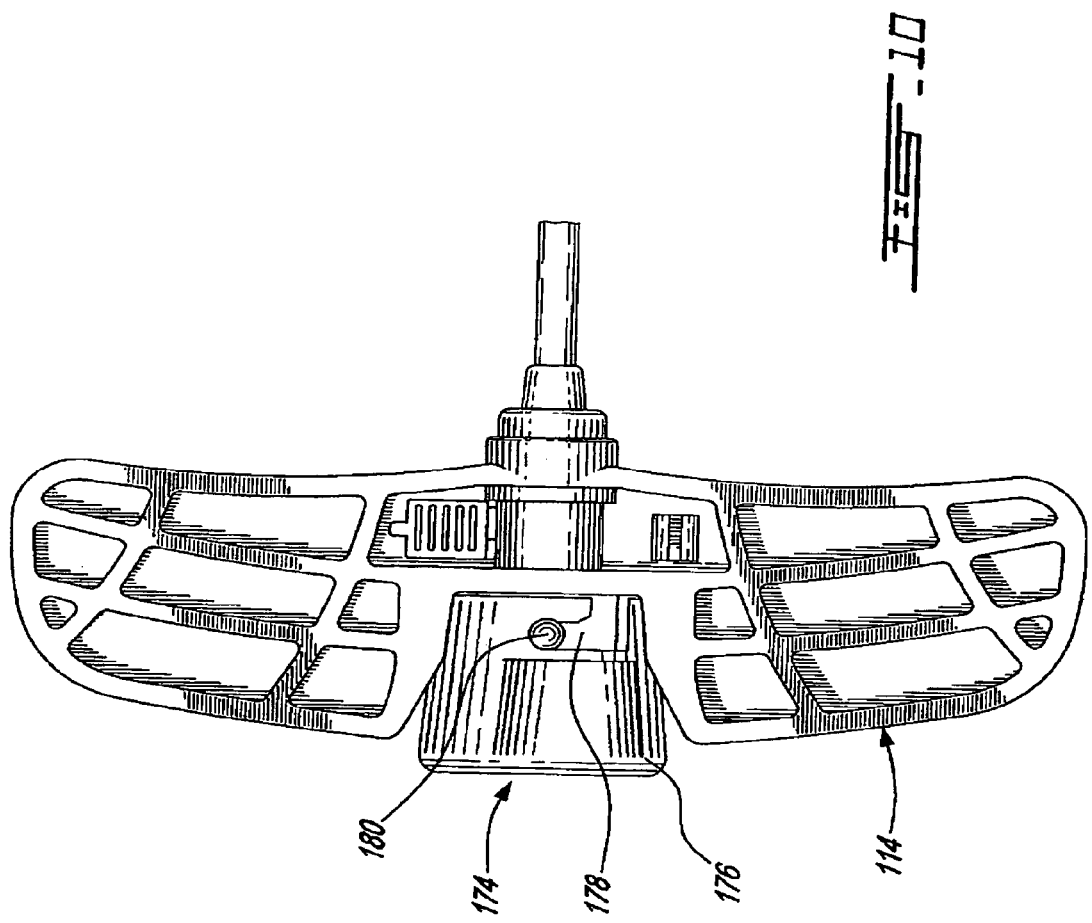
FIG. 10 is a side view of a proximal part of an engaged stylet and outer cannula of the cannula assembly of FIG. 9.

Referring to FIGS. 10-11, the stylet 174 is sized such as to be insertable into the outer cannula 114 when the inner cannula 112 is not inserted therein. The stylet 174 includes a proximal end 176 which has a bayonet slot 178 defined therein. The outer cannula 114 includes, in proximity of its proximal axial port 144, a corresponding radial lug 180 (see FIG. 10) sized and positioned for engagement within the bayonet slot 178. As such, the stylet 174 is inserted through the axial port 144 and rotated for engagement of the lug 180 and bayonet slot 178 prior to the outer cannula 114 being inserted into the bone. The stylet 174 is sized such that its pointed distal tip 182 protrudes from the distal tip 166 of the outer cannula 114 when the two are connected, to facilitate insertion. Once the outer cannula 114 is in place within the bone, the stylet 174 is disconnected and removed, and the inner cannula 112 is inserted into the outer cannula 114 and connected thereto to form a double lumen cannula.

In an alternate embodiment which is not shown, the proximal side port 46, 146 in communication with the peripheral conduit 42, 142 is provided on the connector 16, 116.

In a particular embodiment, the central conduit 22, 122 of the cannula assembly 10, 110 is used to inject bone cement therethrough, for example for a vertebroplasty, while the peripheral conduit 42, 142 is used for aspiration during the bone cement injection.

In a particular embodiment, the cannula assembly 10, 110 is used to deliver bone cement with a cement delivery system such as shown in U.S. patent application Ser. No. 12/246,798 entitled "INTEGRATED CEMENT DELIVERY SYSTEM FOR BONE AUGMENTATION PROCEDURES AND METHODS", which is incorporated by reference herein.

In a particular embodiment, the cannula assembly 10, 110 is used to inject implant material volumes, for example in a vertebroplasty, of about 5 cc, using an injection pressure of at least 1000 psi.

In a particular embodiment, the inner cannula has a size of approximately or exactly 11 or 13 gage, while the outer cannula has a size of approximately or exactly 8 or 9 gage.

The cannula assembly 10, 110 advantageously allows for a double lumen cannula that is relatively easy to manufacture, for example when compared to a single piece double lumen cannula. Also, the cannula assembly 10, 110 provides increased versatility, as inner and outer cannulas 12, 112, 14, 114 of various configurations, e.g. having different sizes and/or patterns and/or locations for the distal openings 34, 134, 62, 162, as well as stylets 174 having various sizes, can easily be combined depending on the requirements of a particular procedure and/or on the patient the procedure is being performed on. In a particular embodiment, a kit may be provided with several inner and outer cannulas of different configurations and/or with stylets of different sizes such that the physician can assemble a customized double lumen cannula as required. The physician can also use the outer cannula as a single lumen cannula, e.g. if no aspiration is required during injection. The connector 16, 116 has a simple configuration and allows the inner and outer cannulas to be easily assembled and disassembled when required.

The embodiments of the invention described above are intended to be exemplary. Those skilled in the art will therefore appreciate that the foregoing description is illustrative only, and that various alternate configurations and modifications can be devised without departing from the spirit of the present invention. Accordingly, the present invention is intended to embrace all such alternate configurations, modifications and variances which fall within the scope of the appended claims.

The invention claimed is:

1. A cannula kit for injecting implant material into a bone, the kit comprising:

a first rigid cannula having a first proximal end and a first tube extending from the first proximal end along a longitudinal axis, the first tube defining a first longitudinal conduit and including a first distal end with at least two first distal openings defined therein in communication with the first conduit, the first proximal end including a first proximal axial port in communication with the first conduit and coaxial therewith, a first connection member adjacent the first proximal port, and at least one proximal side port in communication with the first conduit and located distally of the first connection member, the at least one proximal side port having a central axis different from the longitudinal axis; and a second rigid cannula having a second proximal end and a second tube extending from the second proximal end, the second tube defining a second longitudinal conduit and including a second distal end with at least one second distal opening defined therein in communication with the second conduit, the second tube having an outer diameter smaller than an inner diameter of the first tube, the second tube being insertable in the first tube through the first proximal axial port such that a peripheral conduit is defined between the first and second tubes, the second proximal end including a connector having a second connection member complementary to the first connection member, the complementary connection members together defining a detachable connection between the first and second cannulas;

wherein with the second tube inserted in the first tube and the complementary connection members interconnected, each proximal side port is in communication with the peripheral conduit, at least one of the first distal openings provides communication between the peripheral conduit and an environment outside of the first tube, and each second distal opening provides communication between the central conduit and the environment outside of the first tube through at least one other of the first distal openings.

2. The cannula kit as defined in claim 1, wherein the complementary connection members form a bayonet lock.

3. The cannula kit as defined in claim 1, wherein the central axis of each proximal side port extends at least substantially perpendicularly to the longitudinal axis.

4. The cannula kit as defined in claim 3, wherein there are two proximal side ports extending along the same direction with opposite orientations.

5. The cannula kit as defined in claim 1, wherein the complementary connection members are threadably engaged to one another when the first and second cannulas are interconnected.

6. The cannula kit as defined in claim 1, wherein the connector is detachably connected to the second proximal end.

7. The cannula kit as defined in claim 6, wherein the connector is threadably engaged to the second proximal end.

8. The cannula kit as defined in claim 1, wherein the connector is retained to the second proximal end such as to be freely rotatable with respect thereto.

9. The cannula kit as defined in claim 1, wherein the at least one other of the first distal openings is an open distal tip of the first tube.

10. The cannula kit as defined in claim 9, wherein the at least one second distal opening is an open distal tip of the second tube.

11. The cannula kit as defined in claim 10, wherein the first tube defines an inner shoulder within the peripheral conduit adjacent the open distal tip thereof, the second tube abutting the inner shoulder when the first and second cannulas are interconnected.

12. The cannula kit as defined in claim 10, wherein the distal end of the second tube protrudes beyond the distal end of the first tube through the open distal tip of the first tube when the first and second cannulas are interconnected.

13. The cannula kit as defined in claim 1, wherein the at least one of the first distal openings includes fenestrations defined through a wall of the first tube.

14. The cannula kit as defined in claim 1, further comprising a stylet having a third proximal end including a third connection member complementary to the first connection member or to another connection member provided on the first proximal end adjacent the first connection member, the stylet being sized such as to be insertable within the first tube when the second cannula is removed therefrom.

15. The cannula kit as defined in claim 14, wherein the complementary connection members of the first and third proximal ends form a bayonet lock.

* * * * *